United States Patent [19]

Mazzariello

[11] 4,088,134
[45] May 9, 1978

[54] FORCEPS

[75] Inventor: Rodolpho M. Mazzariello, Buenos Aires, Argentina

[73] Assignee: Joseph A. Caprini

[21] Appl. No.: 711,966

[22] Filed: Aug. 5, 1976

[51] Int. Cl.² ............................................. A61B 17/28
[52] U.S. Cl. ...................................... 128/321; 81/416; 128/319; 128/328; 294/106
[58] Field of Search ................ 128/321, 328, 17, 319, 128/322-324; 294/106; 81/300, 416; 403/121, 119, 353

[56] References Cited

U.S. PATENT DOCUMENTS

| 232,977 | 10/1980 | Judson | 294/106 X |
| 1,528,717 | 3/1925 | Williams | 128/321 X |
| 2,706,921 | 4/1955 | Paulson | 294/106 X |
| 3,921,641 | 11/1975 | Hulka | 128/321 |
| 4,009,507 | 3/1977 | Lascarrou | 403/353 X |

FOREIGN PATENT DOCUMENTS 320,904  12/1902  France ................................. 128/323

Primary Examiner—Robert W. Michell
Assistant Examiner—Michael H. Thaler
Attorney, Agent, or Firm—Wegner, Stellman, McCord, Wiles & Wood

[57] ABSTRACT

A forceps which includes two halves with each half having an elongate body portion with a handle member on one end portion and a distal tip on the other end portion. Spaced hinge parts are carried on the body portion of one half and engage inset recesses formed in the body portion of the other half so that manipulation of the handles will open and close the distal tips relative to each other without changing the exterior size of the combined body portions of the two halves. The two halves are readily separable for sterilization.

3 Claims, 7 Drawing Figures

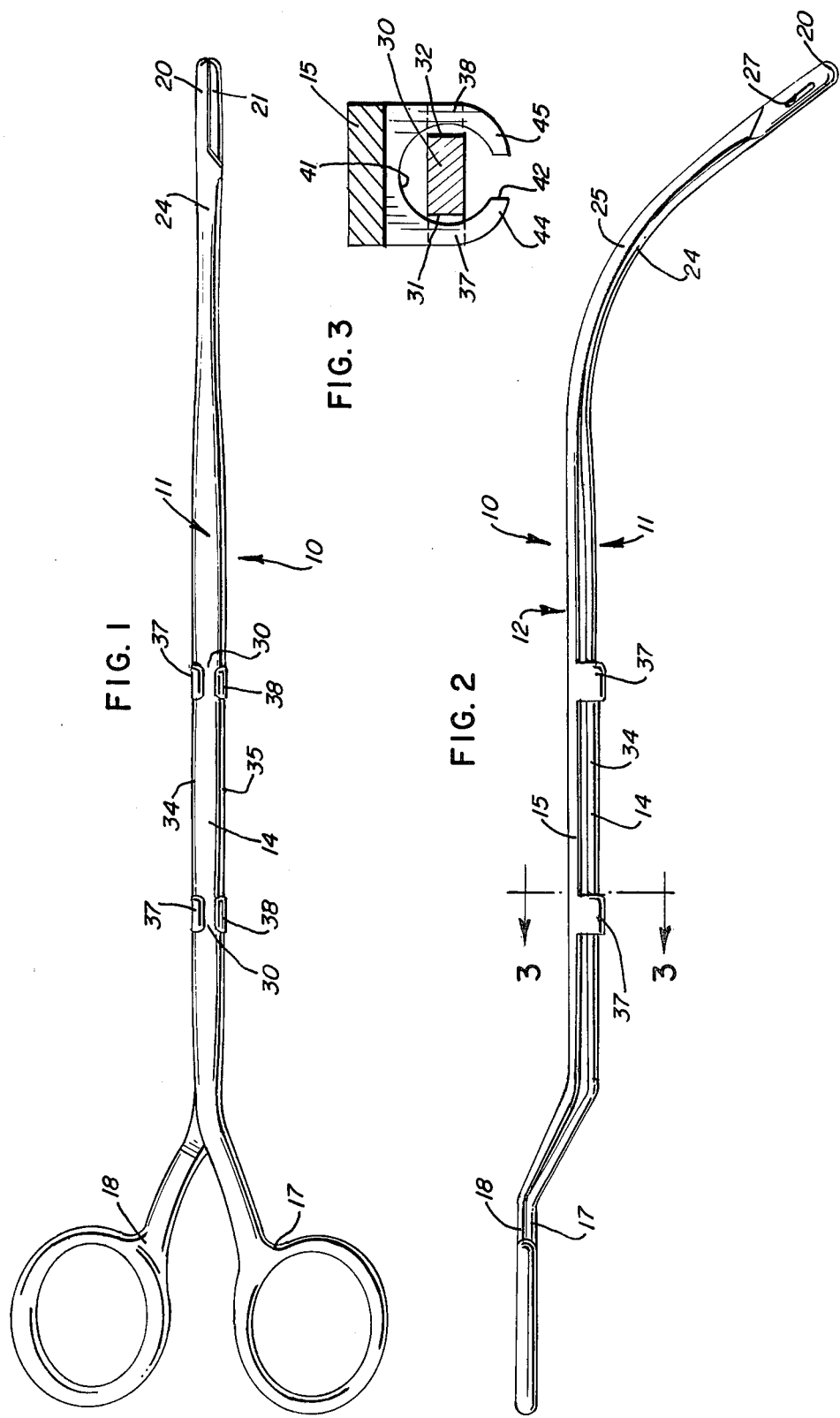

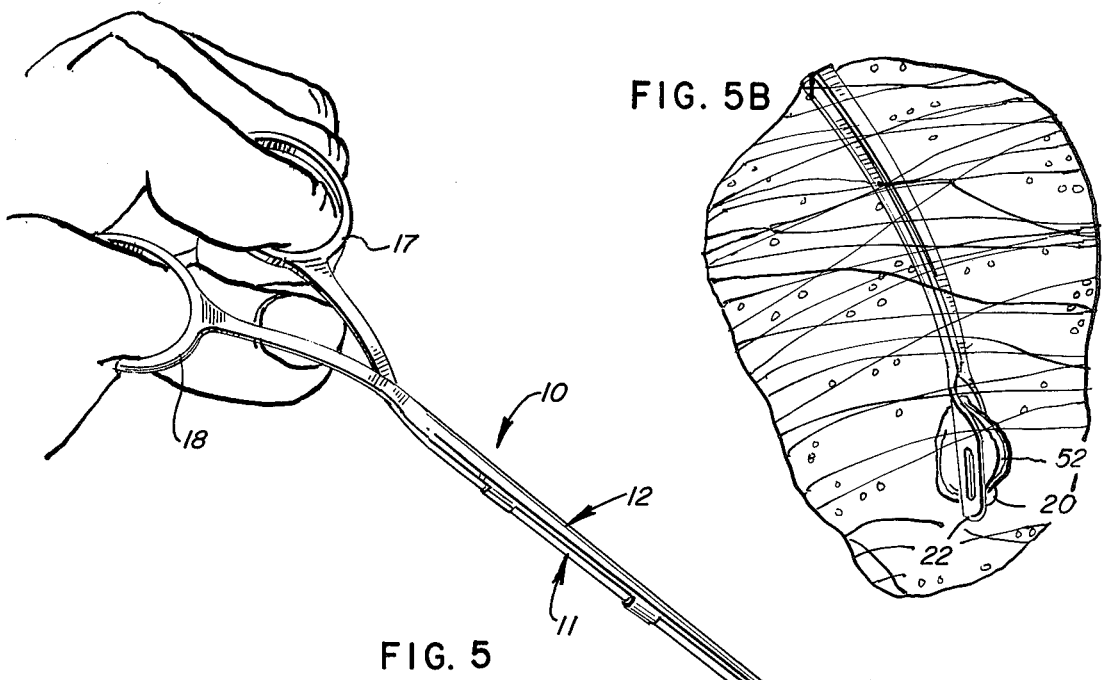
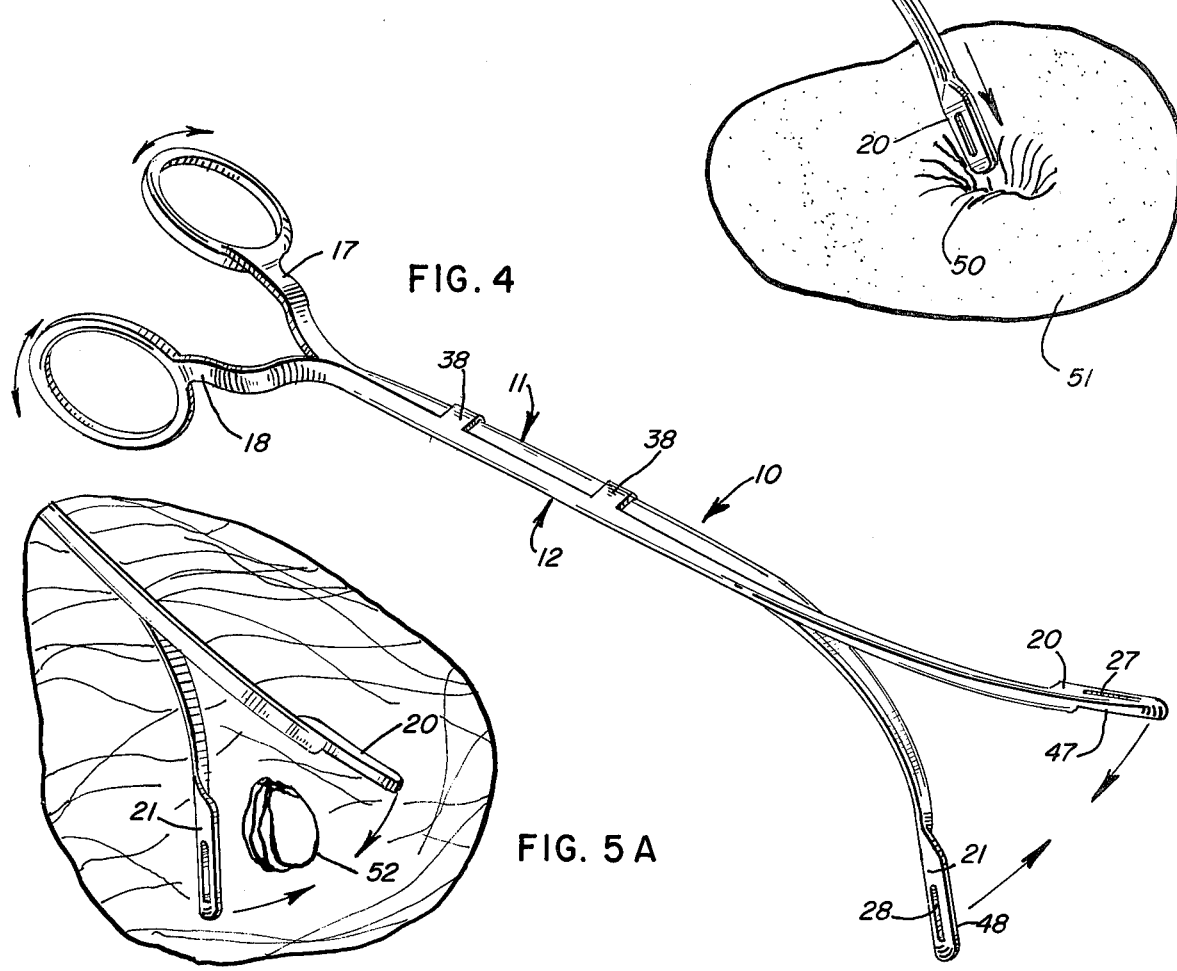

FORCEPS

BACKGROUND OF THE INVENTION

1. Field of the Invention

This invention relates generally to forceps insertable through a small opening and usable without expanding the opening and, more particularly, to surgical forceps in which the tips may be opened and closed without changing the exterior size of the body of the forceps.

2. Description of the Prior Art

In order to decrease unnecessary risk to a patient, it is oftentimes desirable to refrain from undertaking major surgical procedures. Avoiding major surgery by providing out-patient treatment whenever possible, is becoming an increasing practice. Such treatment has been proven to be successful and highly desirable since disruption of the patient's normal activity is lessened.

One area in which major surgery can be avoided is in the removal of common duct stones. Therein, rigid forceps may be required in order to permit passage through a duct system having a midline opening in the sinus tract or in order to crush large stones into easily removable smaller fragments. Since the ducts are often relatively small and since the forceps are inserted a substantial distance into the patient, the forceps must be constructed so that they do not damage the ductal tissues when they are opened and closed. The use of suitable rigid forceps under fluoroscopic control may eliminate the need to make large incisions to remove stones which otherwise may be removed through a relatively small incision with proper manipulation of the forceps.

Forceps for firmly grasping objects are generally constructed by pivotally connecting the body portions between the tips and the handles in a manner similar to that commonly utilized in constructing a pair of pliers. However, the use of forceps of this type is often prevented when the forceps are to be inserted into relatively small passages, since the size of the body of the forceps increases when the tips are opened.

Forceps of a somewhat general character to those of the applicant are shown in Hulka U.S. Pat. No. 3,291,641. Therein, the halves of the forceps are connected together by a hinge assembly like that employed in hanging a door. The construction of the Hulka hinge assembly is much more complex than that shown herein and is more difficult to disconnect for sterilization. In addition, the size of the body increases slightly when tips are closed.

SUMMARY OF THE INVENTION

It is the principal object of the invention to provide a forceps in which the tips may be opened and closed without changing the diameter of the body and which is readily separable for sterilization.

In accordance with the invention, the forceps herein have a pair of elongate shafts, each of which has a handle and a distal tip. One shaft has a pair of side walls defining a longitudinal channel with a narrowed opening. The other shaft has a constricted segment defined by recessed cuts in the sides of the shaft. The constricted segment is placed within the channel between the side walls so that it is nested therein to connect the shafts and permit relative rotation of the shafts to open and close the tips without enlarging the combined intermediate diameter of the forceps.

The forceps constructed according to the invention allows exploration and manipulation of the entire ductal system to be easily accomplished. The forceps of the applicant enables a surgeon to work within the depths of the biliary tree cavity without causing overdistention of the ducts. Dilation of the ducts prior to the insertion of the forceps is often unnecessary because of the narrow configuration of the body of the forceps.

The applicant's forceps are preferred over other surgical instruments when dealing with large stones, impacted stones, or small sinus tracts. The forceps described herein possess tremendous crushing ability so that large or impacted stones may be pulverized between the tips of the forceps and easily removed as smaller fragments.

BRIEF DESCRIPTION OF THE DRAWINGS

The details of construction and operation of the invention are more fully described with reference to the accompanying drawings which form a part hereof and in which like reference numerals refer to like parts throughout.

In the drawings

FIG. 1 is a bottom plan view of the forceps with closed tips;

FIG. 2 is a side elevational view of the forceps shown in FIG. 1;

FIG. 3 is a cross-sectional view of the forceps taken along line 3—3 of FIG. 2 illustrating the connecting assembly in more detail;

FIG. 4 is a perspective view of the forceps with open tips;

FIG. 5 is a perspective view of the forceps with closed tips prior to insertion in the exit wound;

FIG. 5A is a perspective view of the forceps with open tips surrounding a stone within a patient; and FIG. 5B is a perspective view similar to FIG. 5A showing the forceps with partially closed tips grasping a stone.

DESCRIPTION OF THE PREFERRED EMBODIMENT

Referring to FIGS. 1–3, forceps 10 constructed according to the invention includes a pair of shafts 11 and 12 having respective elongate body portions 14 and 15 carrying respective offset handle members 17 and 18, such as finger loops, at their rearward end and cooperating, offset distal tip portions 20 and 21 at their other end. The tips 20 and 21 terminate the respective arcuate forward portions 24 and 25 of the shafts 11 and 12 and have rounded forward ends to prevent inadvertent perforation of sensitive body tissue. The tips 20 and 21 have respective central apertures 27 and 28.

The body portions 14 and 15 of the adjacently disposed shafts 11 and 12 have generally parallel longitudinal axes. As seen in FIG. 2, the longitudinal axes of the body portions 14 and 15 are generally parallel to a horizontal plane extending between the shafts 11 and 12 which plane is equidistant from each axis. The tips 20 and 21 are carried by the shafts 11 and 12 on the same side of the horizontal plane and the handles 17 and 18 are carried on the other side of the horizontal plane.

The shaft 11 has two constricted segments 30 defined by two pairs of inset recesses 31 and 32 formed in the lateral sides 34 and 35 of the shaft 11. As seen in FIG. 3, the constricted segments 30 have a rectangular cross section with the width being greater than the depth.

The shaft 12 has two pairs of laterally spaced side walls 37 and 38 aligned with the constricted segments 30 of the shaft 11 and extend outwardly from the shaft 12 toward the shaft 11. The side walls 37 and 38 define longitudinal channels with bottom walls 41 spaced from the shaft 12 and longitudinal openings 42 at the top of the channels. The channels have a C-shaped cross section similar to a major circular arc with inwardly directed flange portions 44 and 45 to define openings 42 which are narrower than the internal diameter of the channels. The openings 42 have a width greater than the depth of the constricted segments 30 and less than the width of the constricted segments 30. The channels have a length corresponding to the length of the recesses 31 and 32 so that the ends of the constricted segments 30 abut the ends of the channels to prevent relative longitudinal movement between the shafts 11 and 12. The channels also prevent relative pivotal movement between the shafts 11 and 12, while permitting relative rotational movement of the shaft 11 on its longitudinal axis.

The constricted segments 30 may be inserted into the channels by tilting the shaft 11 on its side to permit the constricted segments 30 to pass through the openings 42. Thereafter, the shaft 11 is returned to its usual orientation as shown in FIG. 3 to prevent the constricted segments 30 from passing through the openings 42 by relative movement of the shafts 11 and 12 directly away from each other. The constricted segments 30 are thereby nested within the respective channels so that the shafts 11 and 12 are connected by hinge parts permitting easy disconnection.

As best seen in FIG. 1, shafts 11 and 12 have respective handles 17 and 18 and tips 20 and 21 disposed on opposite sides of a vertical plane containing the longitudinal axes of the shafts 11 and 12, the plane being perpendicular to the horizontal plane. The arcuate forward portions 24 and 25 of the shafts 11 and 12 are twisted slightly so that the tips 20 and 21 present cooperating concave faces 47 and 48 to the vertical plane. As a result, the tips 20 and 21 are closed together when the handles 17 and 18 are moved toward each other and opened when the handles 17 and 18 are moved away from each other. Note that relative motion between the handles 17 and 18 is not linear but arcuate since the shafts 11 and 12 are permitted to rotate about the longitudinal axis of the shaft 11 but are prevented from pivoting relative to one another.

Operation of the forceps 10 is seen in FIGS. 4 and 5. In FIG. 5, the tips 20 and 21 of the forceps 10 are closed to allow insertion of the tips 20 and 21 into an exit wound 50 in the skin 51 of a patient. Once the forceps 10 have been inserted to the desired position, the tips 20 and 21 of the forceps 10 are opened by moving the handles 17 and 18 apart so that the shaft 11 is rotated relative to the shaft 12. When the tips 20 and 21 of the forceps 10 are to be closed around a stone 52 (FIG. 5A), the handles 17 and 18 are moved together as shown by the arrows in FIG. 4. The stone 52 is grasped between the tips 20 and 21 (FIG. 5B) so that when the forceps 10 are removed from the exit wound 50, the stone 52 will also be pulled through the exit wound 50. The stone 52 may be crushed or pulverized into smaller fragments by opening and closing the tips 20 and 21 on the stone 52 until it breaks into smaller pieces whereupon the smaller pieces are individually grasped by the forceps and removed.

If the forceps 10 are firmly held, as shown in FIG. 5, with the thumb passing through the finger loop of the handle 18, the shafts 11 and 12 cannot be inadvertently disconnected, since the shaft 11 is wedged between the channel side walls 37 and 38 by outward pressure of the thumb and finger on the handles 17 and 18.

I claim:

1. A forceps comprising a pair of members each having a handle portion at one end, a distal tip portion at the other end and a body portion extending linearly from the handle portion to the distal tip portion, said body portions having a linear extent greater than either the handle portions or the distal tip portions, said body portions having equal dimensions and being rectangular in cross-section, one of said body portions having an integral segment constricted in a direction perpendicular to the longitudinal axis of said one body portion adjacent each end thereof and the other body portion having a channel forming member adjacent each end thereof, each of said members forming a circular channel having a diameter less than the maximum transverse width of said one body portion and greater than the maximum width of the constricted segments, with the center of said channel being spaced from said other body portion a distance slightly greater than one-half said maximum transverse width of said one body portion, a slot in that portion of the channel forming members most removed from said other body portion said slot having a width approximately equal to the thickness of said one body portion, the distal tip portions being arcuately offset from the body portions and said body portions presenting a unitary structure when said constricted segments are received in said channels.

2. A forceps comprising a pair of members each having a handle portion at one end, a distal tip portion at the other end and a body portion extending linearly from the handle portion to the distal tip portion, said body portions having a linear extent greater than either the handle portions or the distal tip portions, said body portions having equal dimensions and being rectangular in cross-section, one of said body portions having an integral segment constricted in a direction perpendicular to the longitudinal axis of said one body portion adjacent each end thereof and the other body portion having a channel-forming member adjacent each end thereof, each of said members forming a circular channel having a diameter less than the maximum transverse width of said one body portion and greater than the maximum width of the constricted segments, with the center of said channel being spaced from said other body portion a distance slightly greater than one-half said maximum transverse width of said one body portion, the distal tip portions being arcuately offset from the body portions, and said body portions presenting a unitary structure when said constricted segments are received in said channels.

3. A forceps comprising a pair of members each having a handle portion at one end, a distal tip portion at the other end and a body portion extending linearly from the handle portion to the distal tip portion, said body portions having equal dimensions and one of said body portions having a constricted segment adjacent each end thereof and the other body portion having a channel-forming member adjacent each end thereof, each of said members forming a circular channel having a diameter less than the maximum transverse width of said one body portion and greater than the maximum width of the constricted segments, with the center of said channel being spaced from said other body portion a distance slightly greater than one-half said maximum transverse width of said one body portion, the distal tip portions being arcuately offset from the body portions, and said body portions presenting a unitary structure when said constricted segments are received in said channels.

* * * * *